United States Patent [19]

Kloth

[11] Patent Number: 6,108,080
[45] Date of Patent: Aug. 22, 2000

[54] CUVETTE RAIL

[76] Inventor: Bernd Kloth, Mussenredder 8, D-22399 Hamburg, Germany

[21] Appl. No.: 09/171,685

[22] PCT Filed: Apr. 18, 1997

[86] PCT No.: PCT/EP97/01945

§ 371 Date: Nov. 18, 1998

§ 102(e) Date: Nov. 18, 1998

[87] PCT Pub. No.: WO97/40362

PCT Pub. Date: Oct. 30, 1997

[30] Foreign Application Priority Data

Apr. 24, 1996 [DE] Germany ............................ 296 07 461

[51] Int. Cl.[7] .................................................... G01N 21/01
[52] U.S. Cl. .......................................... 356/244; 422/102
[58] Field of Search .................................. 356/244, 246, 356/440, 39; 250/576, 205, 214 C; 327/509, 512–514; 436/43, 47, 48, 49, 54, 174–180; 422/63–67, 100–103

[56] References Cited

U.S. PATENT DOCUMENTS

| 4,639,135 | 1/1987 | Borer et al. . |
|---|---|---|
| 4,787,744 | 11/1988 | Hissung . |
| 5,128,104 | 7/1992 | Murphy et al. . |
| 5,679,948 | 10/1997 | Carey et al. . |
| 5,741,708 | 4/1998 | Carey et al. . |
| 6,016,193 | 1/2000 | Freeman et al. . |

FOREIGN PATENT DOCUMENTS

| 2435317 | 2/1976 | Germany . |
|---|---|---|
| 28 19 820 | 11/1978 | Germany . |
| 29 040597 | 8/1979 | Germany . |
| 92 18 750 U | 4/1995 | Germany . |

*Primary Examiner*—Frank G. Font
*Assistant Examiner*—Tu T. Nguyen

[57] ABSTRACT

In order to provide a cuvet bar (100) for accommodating substances to be optically examined, preferably for use in automated analysis operations, which possesses serially disposed measuring cuvets (11) that are open on one side and interconnected with the aperture area, which guarantees a safe and perfect handling and analysis, it is proposed that the cuvet bar (100) is to possess a handling and mounting member (10) which possesses an essentially cubic basic configuration and in which at least one asymmetrically disposed recess is provided.

30 Claims, 3 Drawing Sheets

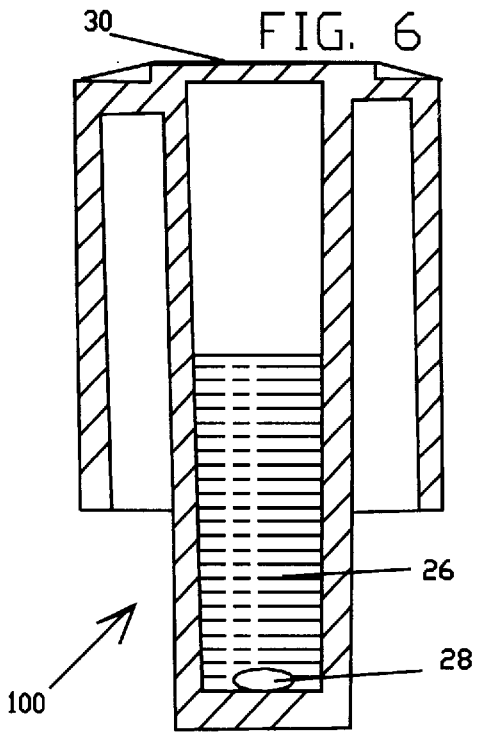
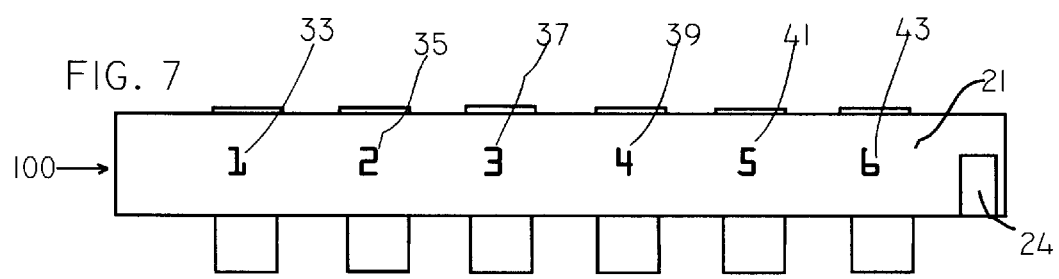
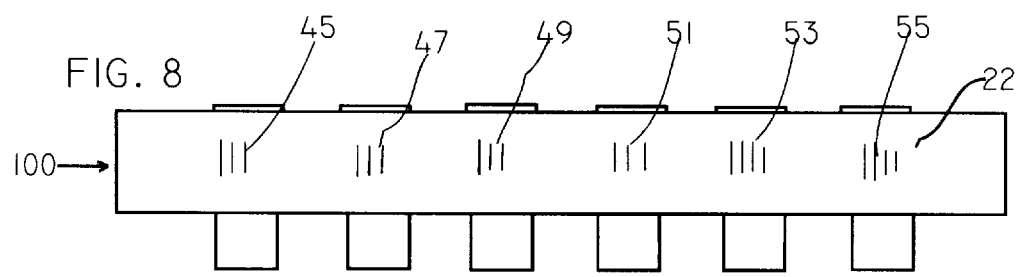

CUVETTE RAIL

TECHNICAL AREA

The invention relates to a cuvet bar for the accommodation of substances to be optically examined, preferably for employment in automated analysis operations, which possesses serially disposed measuring cuvets which are open on one end and interconnected within the aperture area.

Cuvet bars in conformity with the type in question are employed e.g. in the determination of parameters of the blood coagulation system. The performance of the analyses is for the most part and to a great extent effected in an automated manner, in which case the cuvet bar or the measuring cuvets are already provided with reagents and possibly with a stirring member and the measuring cuvets are closed e.g. with the aid of a sealing foil, mostly of aluminium.

For this, several variation possibilities are known. Thus and "endless" cuvet bar has been proposed which, however, ultimately involves measuring cuvets that are interconnected by means of the foil sealing the same. In case of need, the required number of cuvets are severed with the foil.

However, in this case it is disadvantageous that a mounting means is required for the further use of the measuring cuvets, which makes a use and, above everything else, an automated use only possible. In addition, the risk is very great of the foil becoming detached and that individual measuring cuvets become prematurely unserviceable.

A pertinent cuvet bar is described in the U.S. Pat. No. 4,787,744. This cuvet bar is comprised of an elongated cubic member which serves as retaining means and into which the individual measuring cuvets are inserted, one measuring cuvet being in this case disposed so as to be asymmetric in relation to the other measuring cuvets.

In other variants, such as e.g. known from the DE-U 92 18 750, the measuring cuvets are rigidly interconnected, a defined number of measuring cuvets being provided in this instance. In such a case parts of the walls of the measuring cuvets are constructed in the form of a connecting element or the connecting element, surrounding the apertures of the measuring cuvets serves to form a common surface. When the surface is covered with the sealing foil, the apertures of the sealing cuvets are closed.

Also in these cuvet bars the application of the sealing foil proves to be disadvantageous since damage of the foil on the rim side results in at least one measuring cuvet being opned.

Moreover, in all the systems with the exception of the system according to the U.S. Pat. No. 4,787,744, it is not ruled out that, on account of a handling error, an employment of a cuvet bar filled with samples in an analysis apparatus is performed in such a way that the cuvets are not analyzed in the planned sequence, in which connection, in the aforementioned publication, the technical expenditure in the analyzer is uneconomical.

DESCRIPTION OF THE INVENTION, TECHNICAL PROBLEM, SOLUTION, ADVANTAGES

That is why it is the technical problem of the invention to provide a cuvet bar that guarantees a safe and perfect handling and analysis.

The technical problem is resolved by the feature of claim 1.

Furthermore, it is intended to provide a cuvet bar which permits a secure closure of the individual measuring cuvets with a sealing foil, where even damage of the sealing foil on the side of the rim will not lead to an opening of the measuring cuvet itself.

For this, provision is made in accordance with the invention to provide a cuvet bar in conformity with the type in question which possesses a handling and mounting member provided with an essentially cubic basic configuration, in which at least one asymmetrically arranged recess is constructed and wherein cuvets are disposed at uniform intervals and disposed in a symmetric arrangement, in which case the cuvets project from the handling and mounting member with their closed end and, with the rim of their aperture, jut out from the handling and mounting member.

By means of the construction according to the invention it is ensured that each measuring cuvet can be individuallys closed at the rim with a sealing foil, preferably an aluminium foil. The surface of the handling and mounting member protects the sealing foil against damage, in which case, even in the event of the sealing foil being damaged at the rim, no measuring cuvet is opened as the same are sealed at the edge alone.

By preference, the measuring cuvets possess an approximately cylindrical configuration, in which connection basic configurations can be useful. In the cylindrical construction, the same preferably taper somewhat conically towards the sealed end.

The closed side of the measuring cuvets has a flat bottom while, depending upon the construction of the stirring member to be used, also pointed bottoms or suchlike can be made use of.

The cuvet bar is preferably constructed in one piece with the measuring cuvets. For certain application purposes, also a multipart construction proves useful, in which case the handling and mounting member, on its surface, is provided with through bores into which the individual measuring cuvets are insertable and are retained at the edge. Also in the multipart construction, the transfer from handling and mounting member to measuring cuvets takes place via the marginal region.

The handling and mounting member is by preference opened in the downward direction so that the fabrication of the cuvet bar in the form of an injection-moulded part can be readily performed. For the stabilization of the handling and mounting member, webs are disposed between the externally located measuring cuvets and the front ends, which extend across the entire cross-sectional surface area. For an additional strengthening these may be provided with thickened portions.

In order to rule out any confusion of samples in an automated analysis procedure, which may arise when the cuvet bar is introduced in a twisted state into a pertinent device, provision has been made to provide the cuvet bar with asymmetrically disposed recesses, into which corresponding parts of the analysis apparatus engagge, while in this way the conveyance of the cuvet bar in the analysis apparatus is also possible.

For this purpose, a semi-cylindrical indentation may be provided and/or a window disposed in a side wall. Of course, any constructions whatever of the indentations are possible according to the invention so that the cuvet bar can be employed for any apparatus whatever.

For the identification of the individual samples or of the pertinent measuring cuvet, the two side walls of the handling and mounting member can be provided with letterings, in which case optical characters, 33–43 as shown in FIG. 7, are used which can be read by the user and, on the other side, a machine-readable Lettering, e.g. a bar code, 45–55 as shown on FIG. 8, so that, by means of the double identification of the sample, confusions are ruled out, in which case the analysis apparatus displays or prints out the machine-readable lettering at the same time as the analysis data.

Advantageously the measuring cuvets of the cuvet bar may already be provided with reagent fluids and/or with a stirring member so that all that which remains to be added is the fluid to be tested. For this the cuvet bar has, already in its sale model, to be closed with a sealing foil and/or film, the metal foil or plastic film covering each aperture, the foil or film protected on all sides from accidental removal by the handling and mounting member. The foil and/or film can also be a composite material of aluminum foil and plastic film.

The cuvet bar is preferably fabricated from plastic material, such as e.g. polypropylene, polyethylene, polystyrene or the like, the chemical resistance relative to reagents and the optical transmissivity being decisive. For special application purposes, provision is also made for a fabrication from glass.

Further advantegeous constructions are characterized in the subclaims.

BRIEF DESCRIPTION OF THE DRAWINGS

In the following the invention is explained in greater detail with the aid of the drawings. Thus

FIG. 6 shows the sectioned cuvet of FIG. 3 with the orifice covered with a foil and containing a reagent fluid and stirring member.

FIG. 7 shows lettering on one side of the cuvet bar.

FIG. 8 shows a bar code on the other side of the cuvet bar.

BEST WAY OF REALIZING THE INVENTION

Figure 1:
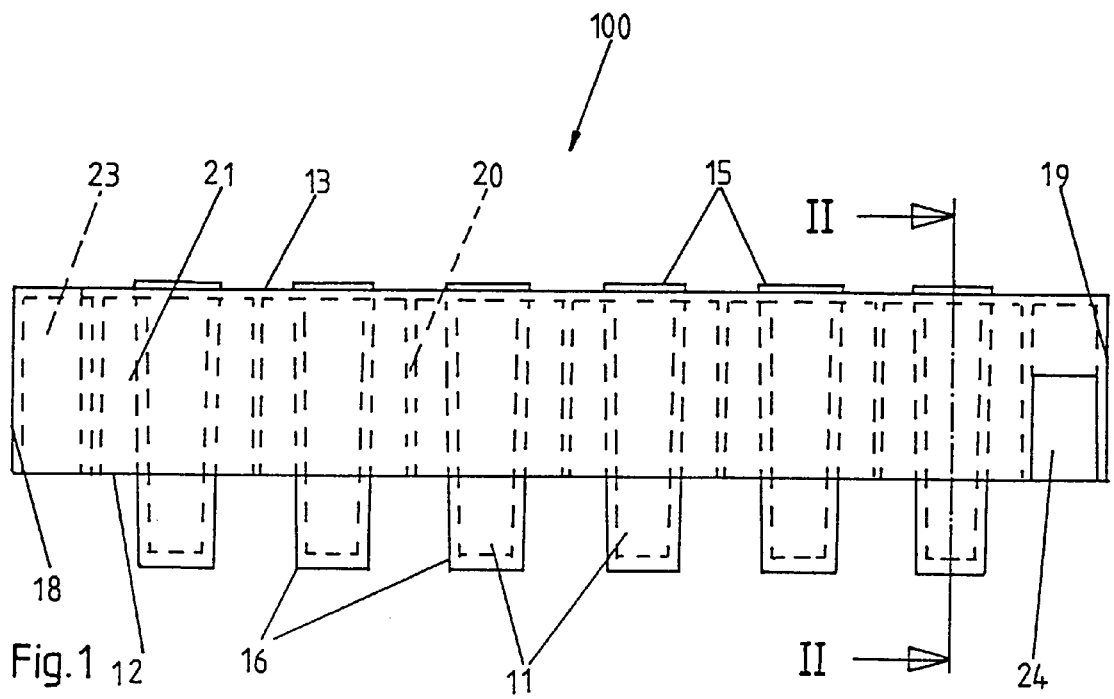
FIG. 1 shows in a side view a side wall of the cuvet bar according to the invention.
Figures 2, 3:
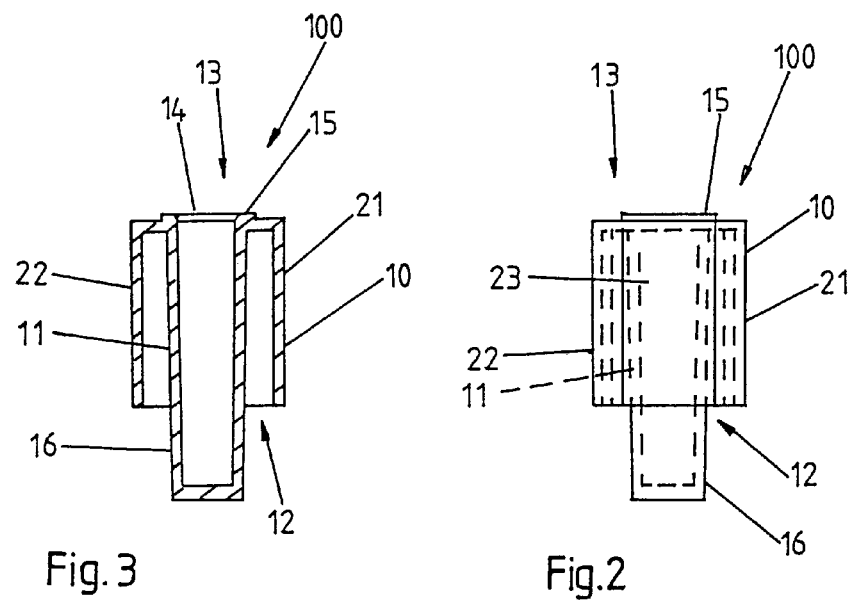
FIG. 2 shows in a side view a front end of the cuvet bar according to the invention.
FIG. 3 shows in a sectioned side view a front end of the cuvet bar according to the invention.
Figure 4:
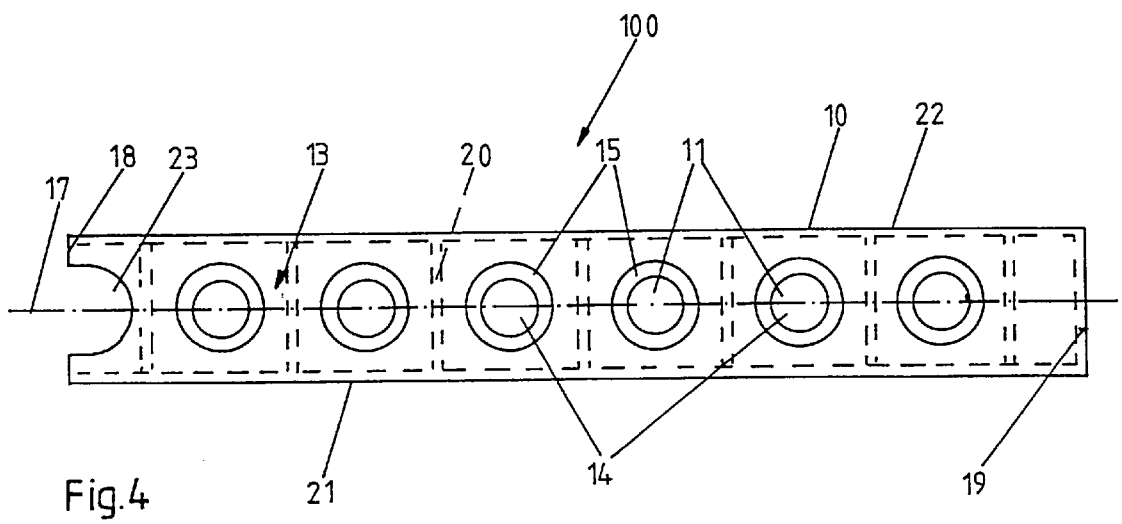
FIG. 4 shows in a view from the top the cuvet bar according to the invention.
Figure 5:
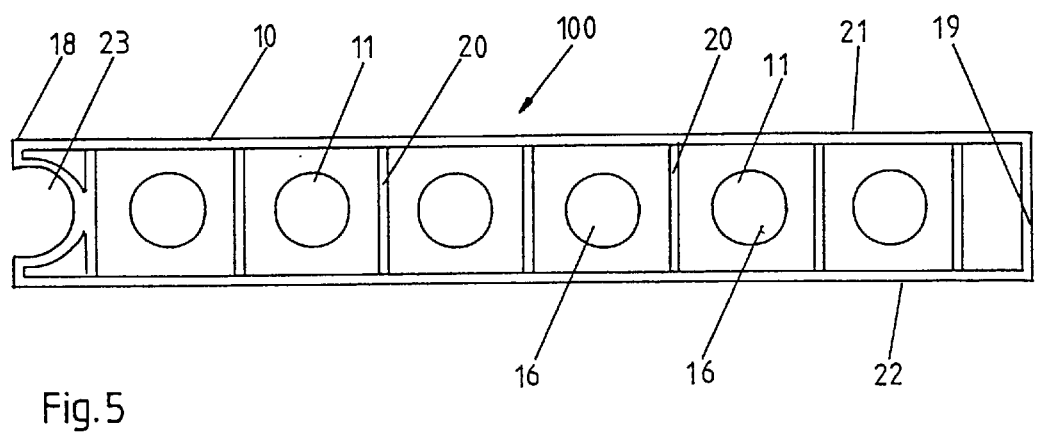
FIG. 5 shows in a view from below the cuvet bar according to the invention.

The cuvet bar 100 is comprised of a handling and mounting member 10 as well as of measuring cuvets 11 disposed in and partly projecting from the same.

The handling and mounting member 10 possesses an essentially cubic basic configuration which, within the region of the underside 12, is constructed so as to be open. On the top side 13 of the handling and mounting member 10, the apertures 14 of the measuring cuvets 11 are provided, in which case the rim 15 of the measuring cuvets 11 projects slightly from the top side 13 of the handling and mounting member 10. The closed side 16 of the measuring cuvets 11 juts out from the open underside 12 of the handling and mounting member 10 in such a way that approximately one third of the measuring cuvet 11 is exposed. The measuring cuvets 11 are arranged centrally along the longitudinal axis 17 of the handling and mounting member 10 and equidistantly from each other. The measuring cuvets 11 located adjacent to the two front ends 18, 19, in the direction of the front ends 18, 19 possess a slightly increased distance than relative to the adjacent other measuring cuvets 11. Between the measuring cuvets 11 and between the externally located measuring cuvets 11 and the respective front ends 18, 19, a web 20 each is provided which extends from the top side 13 to the underside 12 between the two side walls 21, 22 of the handling and mounting member 10. At one front end 18, an approximately semicircular, vertically disposed indentation 23 is provided, which extends nearly as far as to the adjacent web 20. On one front end 21 of the handling and mounting member 10, within the area between one front end 18 and the pertinent web 20, a window 24 is provided in the wall, which extends from the underside 12 to approximately two thirds of the height of the handling and mounting member 10. The measuring cuvets 11 are essentially configured so as to be cylindrical, however, in the direction of the closed side 16, they taper slightly conically. The connection of the measuring cuvets 11 with the handling and mounting member 10 is realized within the region of the rim 15 of the measuring cuvets 11.

As is shown in FIG. 6 the measuring cuvets 11 are provided with reagent fluids 26 and/or with a stirring member 28 so that all that remains to be added is the fluid to be tested. The cuvets 11 are closed at the top with a sealing foil and or film 30, in this particular instance the foil is aluminum foil 30.

As is shown in FIG. 7, side wall 21 is marked with optical characters 33, 35. 37, 39. 41, and 43 to identify individual cuvets. As is shown in FIG. 8, side wall 22 is marked with bar codes 45, 47, 49, 51, 53, and 55 which provides machine readable lettering to provide double identification of each sample in each cuvet.

| LIST OF REFERENCE NUMBERS | |
|---|---|
| Cuvet bar | 100 |
| handling and mounting member | 10 |
| measuring cuvet | 11 |
| underside | 12 |
| top side | 13 |
| aperture | 14 |
| rim | 15 |
| closed side | 16 |
| Longitudinal axis | 17 |
| front end | 18, 19 |
| web | 20 |
| side wall | 21, 22 |
| indentation | 23 |
| window | 24 |
| reagent fluids | 26 |
| stirring member | 28 |
| aluminum foil | 30 |
| optical characters | 33–43 |
| bar code | 45–55. |

What is claimed is:

1. A cuvet bar (100) for the accommodation of substances to be optically examined, preferably for use in automated analysis apparatus, which possesses measuring cuvets disposed in series that are open at one end and interconnected within an aperture region, characterized in that
   a) the cuvet bar (100) is provided with a handling and mounting member (10), which possesses an essentially cubic basic configuration, wherein at least one asymmetrically disposed indentation is to be found, into which indentation a corresponding part of the analysis apparatus engages, the cuvet aperture region jutting above the mounting member and
   b) a metal foil or plastic film covering each cuvet aperture, the foil or film protected on all sides from accidental removal by the handling and mounting member.

2. Cuvet bar according to claim 1, characterized in that, in the handling and mounting member (10), measuring cuvets (11) are disposed at uniform intervals and in symmetrical arrangement, in which case the measuring cuvets (11) project with their closed side (16) from the handling and mounting member (10) and in that the measuring cuvets (11) project with the rim (15) of their aperture (14) above the handling and mounting member (10).

3. Cuvet bar according to claim 1 characterized in that the asymmetrically disposed indentation is comprised of a semi-circular indentation (23) on one of the front ends (18,19) of the handling and mounting member (10).

4. Cuvet bar according to claim 1, characterized in that the asymmetrically disposed indentation is comprised of a window (24) disposed within a marginal area of a side wall (21,22) of the handling and mounting member (10).

5. Cuvet bar according to claim 1 characterized in that several asymmetrically disposed recesses are provided in the cuvet bar (100).

6. Cuvet bar according to claim 1 characterized in that the handling and mounting member (10) is constructed so as to be hollow and open on an underside (12).

7. Cuvet bar according to claim 1 characterized in that the measuring cuvets (11), with a closed side (16), project with approximately one third their total length from an underside (12) of the handling and mounting member (10).

8. Cuvet bar according to claim 1 characterized in that, between measuring cuvets (11) and externally located measuring cuvets (11) and front ends (18,19), a web (20) is disposed in each case.

9. Cuvet bar according to claim 8, characterized in that the web (20) proceeds parallel to the front ends (18,19) and so as to take up cross-sectional area or a part of the cross-sectional area of the handling and mounting member (10).

10. Cuvet bar according to claim 1 characterized in that the measuring cuvets (11) possess a cylindrical cross section.

11. Cuvet bar according to claim 1 characterized in that the measuring cuvets (11) possess an angular cross section.

12. Cuvet bar according to claim 1 characterized in that the measuring cuvets (11) possess areas having different cross-sectional profiles.

13. Cuvet bar according to claim 1 characterized in that the measuring cuvets (11), in the direction of closed side (16), taper slightly conically.

14. Cuvet bar according to claim 1 characterized in that a closed side (16) of the measuring cuvets (11) possesses a flat bottom.

15. Cuvet bar according to claim 1 characterized in that a closed side (16) of the measuring cuvets (11) possesses a three-dimensionally configured bottom.

16. The cuvet bar according to claim 1 characterized in that the cuvet bar (100) including the handling and mounting member (10) is comprised of one piece.

17. The cuvet bar according to claim 1 characterized in that the cuvet bar is comprised of the handling and mounting member (10) which, on its top side (13), is provided with apertures wherein the measuring cuvets (11) are clampingly retained in their rim area.

18. Cuvet bar according to claim 1 characterized in that the cuvet bar (100) possesses an even number of measuring cuvets (11).

19. Cuvet bar according to claim 1 characterized in that the cuvet bar (100) possesses an odd number of measuring cuvets (11).

20. Cuvet bar according to claim 1 characterized in that side wall (21,22) are provided with optical characters and/or machine-readable lettering, such as a bar code.

21. Cuvet bar according to claim 1 characterized in that the cuvet bar (100) is comprised of plastic selected from the class comprising polypropylene, polyethylene, polystyrene or suchlike.

22. Cuvet bar according to claim 1 characterized in that the cuvet bar is comprised of glass.

23. Cuvet bar according to claim 1 characterized in that a cuvet part (100) is an injection-molded part.

24. Cuvet bar according to claim 23, characterized in that the bottom of the measuring cuvets (11), on their exterior, carry one sprayed-on point each.

25. Cuvet bar according to claim 1 characterized in that the measuring cuvets (11), in the side of their rims, are closed by means of a sealing foil.

26. Cuvet bar according to claim 25, characterized in that the sealing foil is comprised of alumimium.

27. Cuvet bar according to claim 25, characterized in that the sealing foil is comprised of plastic.

28. Cuvet bar according to claim 25, characterized in that the sealing foil is comprised of a composite material of aluminium and plastic foil.

29. A cuvet bar according to claim 1 characterized in that the measuring cuvets (11) are provided with reagent fluid.

30. A cuvet bar according to claim 1 characterized in that a stirring member is incorporated into the measuring cuvets (11).

* * * * *